United States Patent
Mrochen et al.

(10) Patent No.: US 8,029,500 B2
(45) Date of Patent: Oct. 4, 2011

(54) CONTROL PROGRAM AND METHOD FOR OPHTHALMOLOGIC SURGERY

(75) Inventors: Michael Mrochen, Nanikon (CH); Olaf Kittelmann, Berlin (DE); Christof Donitzky, Eckental (DE); Rafael Zatonski, Nuremberg (DE)

(73) Assignee: Wavelight GmbH, Erlangen (DE)

( * ) Notice: Subject to any disclaimer, the term of this patent is extended or adjusted under 35 U.S.C. 154(b) by 240 days.

(21) Appl. No.: 11/686,208

(22) Filed: Mar. 14, 2007

(65) Prior Publication Data

US 2008/0051769 A1 Feb. 28, 2008

(30) Foreign Application Priority Data

Mar. 15, 2006 (EP) .................................... 06005317

(51) Int. Cl.
*A61B 18/20* (2006.01)
(52) U.S. Cl. .................. 606/5; 606/4; 606/10; 128/898
(58) Field of Classification Search .................. 606/4–6, 606/10–12; 128/898; 351/205–212
See application file for complete search history.

(56) References Cited

U.S. PATENT DOCUMENTS

| | | | | |
|---|---|---|---|---|
| 6,428,533 | B1 * | 8/2002 | Bille | 606/11 |
| 6,451,006 | B1 * | 9/2002 | Bille | 606/5 |
| 6,641,577 | B2 * | 11/2003 | Bille | 606/4 |
| 6,887,231 | B2 * | 5/2005 | Mrochen et al. | 606/5 |
| 7,083,609 | B2 * | 8/2006 | Chernyak | 606/5 |
| 7,189,224 | B2 * | 3/2007 | Kurtz et al. | 606/5 |
| 7,232,436 | B2 * | 6/2007 | Bille | 606/5 |
| 2002/0193704 | A1 | 12/2002 | Goldstein et al. | |
| 2004/0243112 | A1 | 12/2004 | Bendett et al. | |

FOREIGN PATENT DOCUMENTS

| | | |
|---|---|---|
| EP | 1138291 A2 | 10/2001 |
| WO | WO02076320 A1 | 10/2002 |

OTHER PUBLICATIONS

Juhasz, et al. "Corneal Refractive Surgery with Femtosecond Lasers" IEEE Journal of Selected Topics in Quantum Electronics, vol. 5, No. 4 (Jul./ Aug. 1999).

Heisterkamp, et al. "Optimierung der Laserparameter fur die instrastromale Schnittfuhrung mittels ultrakurzer Laserpulse," Paper No. XP-002368976, Der Opthalmologe, vol. 98, pp. 623-628, Springer-Verlag (2001).

Perry S. Binder, "Flap Dimensions Created With the IntraLase FS Laser," Journal of Cataract Refractive Surgery 2004, 30:26-32, pp. 26-32.

European Office Action dated Dec. 18, 2008 issued in German patent application No. 06005317.0, 4 pages.

European Office Action dated May 20, 2010 issued in German patent application No. 06005317.0, 4 pages.

* cited by examiner

*Primary Examiner* — Ahmed M Farah
(74) *Attorney, Agent, or Firm* — Haynes and Boone, LLP

(57) ABSTRACT

The present invention relates to a method for generating a control program for ophthalmologic LASIK surgery, with which a pulsed laser system (12, 14, 16) can be controlled for the photodisruptive cutting of a flap, having the following steps:
obtaining empirical data, which relate to the effect in particular of flap shapes and ablation profiles on postoperative refractive results,
obtaining measurement data relating to the eye to be treated,
calculating an optimal cutting shape for the photodisruptive cutting of the flap by taking into account the said empirical data and the said measurement data, and
generating the control program on the basis of the calculated cutting shape.

18 Claims, 2 Drawing Sheets

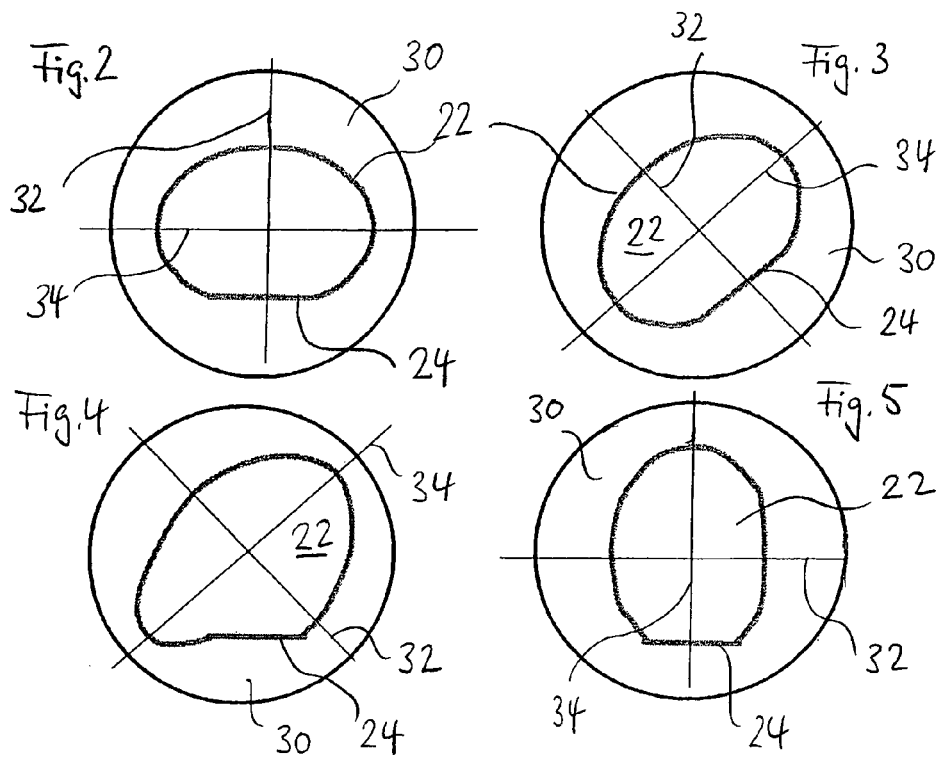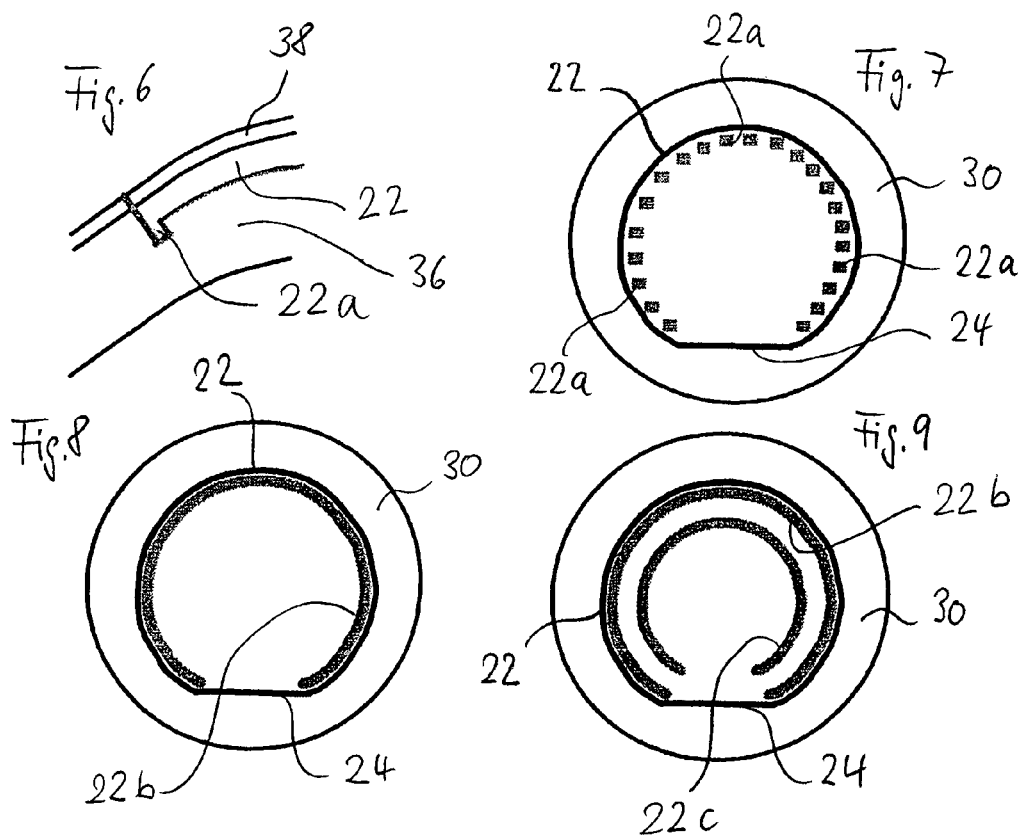

CONTROL PROGRAM AND METHOD FOR OPHTHALMOLOGIC SURGERY

Figure 1:
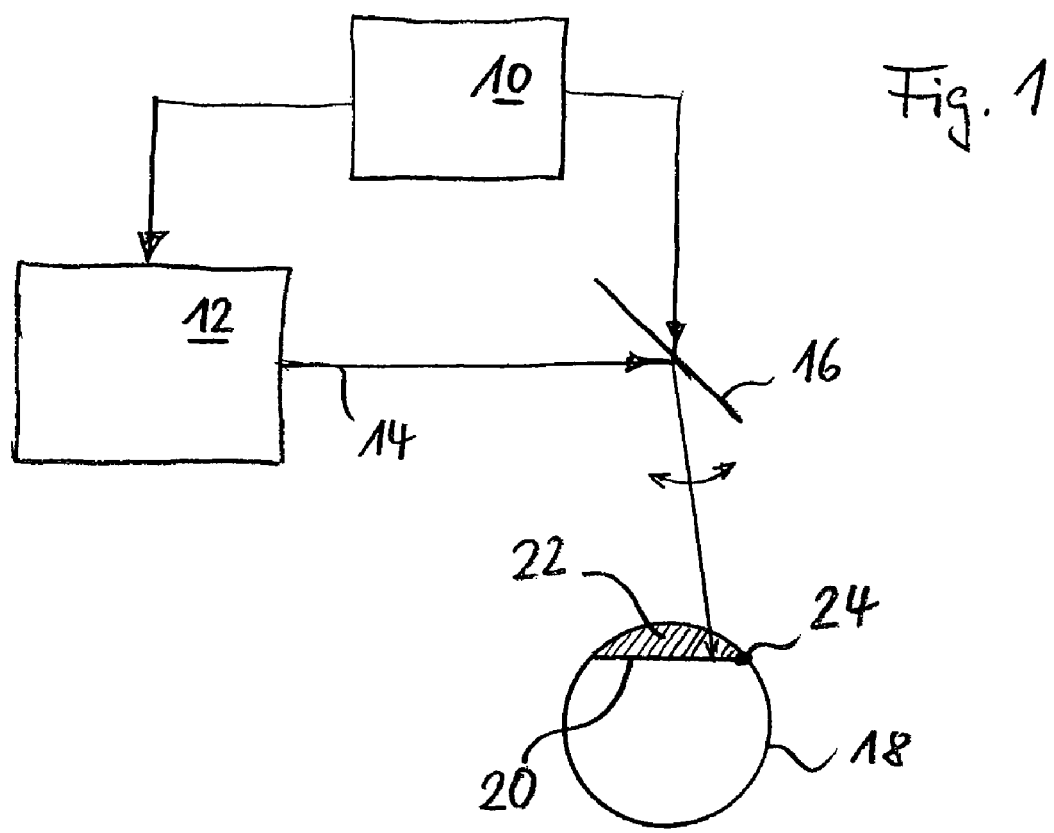

The invention relates to a method for generating a control program for ophthalmologic surgery, to control programs for ophthalmologic surgery, to a computer for controlling an ophthalmologic laser system, and to a data medium having control programs for ophthalmologic surgery.

The invention will be explained below with a view to the known LASIK method.

In the ophthalmologic LASIK method, undesired imaging properties of the eye are removed or at least reduced by reshaping the cornea.

Conventionally, in the LASIK method, a so-called flap is formed on the front side of the cornea and folded to the side. In a second step, corneal tissue is removed according to a so-called ablation profile in the stroma thus exposed. The flap, which has remained joined to the cornea at a so-called hinge, is then folded back and relatively rapid healing of the tissue takes place.

In order to generate the flap, essentially two techniques are currently available:

On the one hand, an oscillating blade is mechanically guided through the corneal tissue with a so-called microkeratome in order to form the flap.

According to a more advanced method, a laser is also used for generating the flap. To this end in particular FS lasers (femtosecond lasers) are used, the radiation of which is focused in the stroma below the surface of the cornea so as to photodisruptively cause tissue separation at a multiplicity of adjacent positions there. This photodisruptive process is also referred to as LIOB (Laser-Induced Optical Breakdown) (cf. Juhasz et al. "CORNEAL REFRACTIVE SURGERY WITH FEMTOSECOND LASERS", IEEE Journal of Selected Topics in Quantum Electronics, Vol. 5, No 4, July/August 1999). If the focusing of the laser pulses leads to a sufficient power density (energy per unit time and area), which lies above a particular threshold value, then the photodisruptive process takes place with sufficient quality i.e. smoothness of the cut and accuracy in respect of the desired shape. In order to achieve the high intensities necessary for this, ultrashort laser pulses are generally required i.e. laser pulses in the femtosecond range, this term conventionally covering pulse lengths shorter than one picosecond i.e. pulse lengths of between 1 femtosecond and 999 femtoseconds. The focusing of the laser beam is then generally carried out in the micrometer range.

It is an object of the invention to provide means with which improved ophthalmologic surgical treatment results can be achieved.

To this end, the invention provides a method for generating a control program for ophthalmologic LASIK surgery, with which a pulsed laser system can be controlled for the photodisruptive cutting of a flap, wherein the program is obtained by the following steps:

obtaining empirical data, which relate to the effect in particular of flap shapes and ablation profiles on postoperative refractive results, obtaining measurement data relating to the eye to be treated, calculating an optimal cutting shape for the photodisruptive cutting of the flap by taking into account the said empirical data and the said measurement data, and generating the control program on the basis of the calculated cutting shape.

The invention thus makes use in particular of the discovery that flap shapes often have an effect on the refractive treatment result i.e. the ability of the treated eye, after its local refraction properties have been modified, to generate sharp images on the retina or the fovea. In LASIK operations, a so-called ablation profile is generally calculated by known techniques. The invention adapts in particular the flap diameter or other dimensions of the flap (in particular depth) to the ablation profile. Particularly in the case of myopic or hyperopic astigmatisms, it is advantageous for the flap to have a sufficient diameter in particular axes, including the transition zone. In other words: in case of a multiplicity of indications, a flap which is not axisymmetric (circular) is optimal.

The invention is thus based on the further discovery that individually adapted cutting shapes in respect of the flap can be significant with regard to the refractive end result after healing of the flap with the stroma.

The invention therefore also provides a control program for ophthalmologic surgery, with which a pulsed laser system can be controlled for the photodisruptive cutting of a flap, wherein the control program provides different flap diameters for cutting in different axes.

The two aforementioned axes are in this case preferably mutually perpendicular. One of the axes conventionally (but not always) extends parallel to the so-called hinge of the flap, i.e. the position where the flap remains joined to the corneal tissue. This hinge could also be referred to as a "pivot" or "articulation".

Another variant of the invention provides a control program for ophthalmologic LASIK surgery, with which a pulsed laser system can be controlled for the photodisruptive cutting of a flap, wherein the control program provides one or more projections in the flap shape, by which the flap can be anchored in the corneal tissue after it is folded back.

Particular configurations of this variant of the invention provide tooth-shaped or horseshoe-shaped projections.

The invention provides the obtaining of empirical data, which relate to the effect in particular of flap shapes and ablation profiles on the postoperative refractive result. This means that the refractive results, which are finally obtained with different cutting shapes, are evaluated in the scope of clinical studies and empirical discoveries are subsequently obtained therefrom. In this way, in particular, higher-order optical aberrations can be minimised by suitable shaping for the flap diameter, in particular by a flap circumference configuration which is not circularly axisymmetric (these definitions leaving out the hinge region of the flap, which trivially is not circularly axisymmetric).

Another variant of the invention provides a control program for ophthalmologic LASIK surgery, wherein a the control program provides for the flap diameter to be smaller than a stromal bed, into which the flap is folded back.

The two aspects of the invention dealt with above, i.e. the projections for anchorage and forming the flap diameter smaller than the stromal bed into which the flap is folded back, address in particular the problem of so-called flap shrinkage and the concomitant creasing.

Shrinkage directly after cutting or displacement of the flap by biomechanical affects can lead to extremely undesirable postoperative faults in the flap. Generating fixation points and edges by means of the said projections counteracts such faults. It is furthermore conducive to folding the flap back true-to-shape.

In contrast to using a mechanical microkeratome, the control of laser pulses allows three-dimensional shaping for the flap and, concomitant therewith, also three-dimensional shaping in the edge region of the remaining stroma bed, which can remain unmodified during the subsequent ablation if the shapes intended for fixation lie outside the refractive ablation profile.

The shrinkage process generally plays a part only in the early postoperative phase. After the flap has been rehydrated, particularly in the case of relatively high myopia corrections or myopic astigmatisms, it is found that the flap does not fit the remaining stromal bed. For this case, the invention therefore provides a control program which, at least in particular regions, makes the flap diameter smaller than the associated diameter of the stromal bed.

The invention also provides a computer programmed with the described control program, which controls a pulsed laser system in a manner known per se, for example by the galvanometer principle.

Exemplary embodiments of the invention will be explained in more detail below with the aid of the drawing, in which:

FIG. 1 schematically shows a device for ophthalmologic surgery, in particular LASIK, FIGS. 2 to 5 schematically show exemplary embodiments of flap cutting shapes;

FIGS. 6 to 9 schematically show exemplary embodiments of flap cutting shapes with anchoring means.

FIG. 1 shows a system for ophthalmologic LASIK surgery having a computer 10 and a laser 12, which emits a laser beam 14 pulsed in the femtosecond range. The computer 10 controls both the laser 12 and a galvanically movable mirror 16, by which the laser beam is directed onto the eye 18 to be treated. The laser beam is focused in a manner known per se on the position where the cut 20 is made in order to generate the flap 22. The flap 22, which remains joined to the corneal tissue via a hinge 24, is then formed by the photodisruptive effect as described above. This per se is prior art.

FIGS. 2 to 5 show individual flap shapes, as a function of individual indications.

FIGS. 2 to 5 respectively show a cornea 30 in plan view. The contours of the flap are denoted by the reference numeral 22. The hinge 24 is generally straight, as can be seen respectively in FIGS. 2 to 5.

FIGS. 2 to 5 furthermore show mutually perpendicular axes, namely a steep axis 32 and a flat axis 34. The steep axis corresponds to the direction over the flap in which there are steeper (stronger) curvatures, and the flat axis the direction over the flap in which there are weaker curvatures.

FIGS. 2 to 5 relate to an astigmatism correction with individual flaps. FIG. 2 shows a flat axis in the horizontal direction in the case of an inferior hinge. In FIG. 3 the flat axis (34) is rotated by 30°+, as is the hinge 24. In the example according to FIG. 4, there is again an inferior hinge and the flat axis is rotated by 30°+.

Lastly, FIG. 5 again shows an inferior hinge, with a flat axis which extends vertically and is perpendicular to the hinge 24.

FIGS. 2 to 5 show typical individually adapted flap shapes which, for particular empirically determined indications and associated corresponding ablation profiles, provide an optimal refraction result after healing.

Input parameters for this method are, in particular, biometric data of the cornea of the epithelium (thickness distribution) and of the anterior eye section (for example anterior chamber depth, corneal refractive index etc.). Typical input parameters are furthermore biomechanical measurement results from various measurement methods, for example Poisson's ratio, Young's modulus, as well as data regarding the elastic, in particular viscoelastic behaviour of the cornea. In particular, empirically obtained data relate to the epithelial smoothing in the postoperative period as well as to the ablation profile used.

Output data, i.e. the "obtained empirical data", relate to variations in the diameter and the thickness of the flap as a function of the said ablation profile. This has, in particular, the purpose of minimising optical aberrations induced by the operation or existing. Output data are furthermore a mathematical or discrete description of the flap in a matrix with three space coordinates and a specification for the chronological sequence of the cutting in order to minimise aberrations. The data are preferably taken into account in a nomogram.

FIG. 6 shows a particular configuration of a flap 22 with a tooth-shaped projection 22a for anchoring in the stroma 36 of the cornea. The epithelium 38 is furthermore represented. FIG. 6 shows a section through a subregion of the cornea, where the anchoring tooth 22a acts. FIG. 7 shows a plan view of the same cornea 30 with a multiplicity of teeth 22a, which extend along the circumference of the flap 22 apart from the region of the hinge 24, where no anchoring is necessary because the corneal tissue remains intact. FIGS. 8 and 9 respectively show a plan view of a cornea 30 and a flap 22. In the exemplary embodiment according to FIG. 8, an approximately horseshoe-shaped projection 22b is provided which, in section, appears like the tooth-shaped projection 22a according to FIG. 6. With the horseshoe-shaped projection 22b according to FIG. 8, circumferential anchoring in the stroma bed is thus carried out on the edge of the flap 22. In the exemplary embodiment according to FIG. 9, two concentric horseshoe-shaped anchoring projections 22b, 22c are provided.

The invention claimed is:

1. A method for generating and utilizing a control program for ophthalmologic LASIK surgery, with which a pulsed laser system can be controlled for the photodisruptive cutting of a flap, having the following steps:
    obtaining empirical data, which relate to the effect in particular of flap shapes and ablation profiles on postoperative refractive results,
    measuring measurement data relating to the eye to be treated,
    calculating an optimal cutting shape for the photodisruptive cutting of the flap by taking into account the said empirical data and the said measurement data using a computer,
    generating the control program on the basis of the calculated cutting shape using a computer, and
    utilizing the control program to control a pulsed laser system to photodisruptively cut the flap wherein a shape of the flap has an effect on refractive results of the eye.

2. The method of claim 1, characterised in that the generated control program provides different flap shapes, in particular flap diameters and/or flap depths, for cutting in different axes.

3. The method according to claim 2, characterised in that the axes are mutually perpendicular.

4. The method according to claim 2, characterised in that one of the axes is essentially perpendicular to a hinge of the flap.

5. The method of claim 2, characterised in that the control program provides one or more projections in the flap shape, by which the flap can be anchored in the corneal tissue after it is folded back.

6. The method according to claim 5, characterised in that the one or more projections are tooth-shaped.

7. The method according to claim 5, characterised in that at least one of the one or more projections has the shape of an unclosed ring.

8. The method according to claim 2, characterised in that the control program provides for the flap diameter to be smaller than a stromal bed, into which the flap is folded back.

9. The method of claim 1, wherein the optimal cutting shape is calculated to be not axisymmetric.

10. The method of claim 9, wherein the optimal cutting shape is calculated to include one or more projections for anchoring in the corneal tissue.

11. A method of performing eye surgery, comprising:
obtaining empirical data related to effects of flap shapes and ablation profiles on postoperative refractive results;
obtaining measurement data relating to an eye to be treated;
calculating an optimal cutting shape for cutting a flap on the eye to be treated by taking into account the empirical data and the measurement data;
generating a control program for controlling a pulsed laser system for photo-disruptive cutting of the flap based on the calculated cutting shape; and
cutting the flap using a pulsed laser system controlled by the generated control program wherein a shape of the flap has an effect on refractive results of the eye.

12. The method of claim 11, wherein the optimal cutting shape is calculated to be not axisymmetric.

13. The method of claim 12, wherein the optimal cutting shape is calculated to include one or more projections for anchoring in the corneal tissue.

14. The method of claim 13, wherein at least one of the one or more projections is tooth-shaped.

15. The method of claim 13, wherein at least one of the one or more projections is horseshoe-shaped.

16. The method of claim 11, wherein the optimal cutting shape is calculated such that the flap has a diameter smaller than a stromal bed into which the flap is folded back into.

17. The method of claim 11, wherein the obtaining measurement data comprises obtaining biometric data related to a cornea of the eye.

18. The method of claim 17, wherein the biometric data related to the cornea comprises a thickness distribution.

* * * * *